United States Patent [19]
Fritzberg et al.

[11] Patent Number: 5,059,541
[45] Date of Patent: Oct. 22, 1991

[54] MINIMAL DERIVATIZATION OF PROTEINS

[75] Inventors: Alan R. Fritzberg; Daniel S. Wilbur, both of Edmonds; Ananthachari Srinivasan, Kirkland; Dennis W. Wester, Lynnwood, all of Wash.

[73] Assignee: Neorx Corporation, Seattle, Wash.

[21] Appl. No.: 187,714

[22] Filed: Apr. 29, 1988

[51] Int. Cl.$^5$ .......................................... G01N 33/566
[52] U.S. Cl. .................................... 436/501; 436/547; 436/548; 436/804; 436/819; 436/518; 435/188; 530/387; 530/402; 530/405; 530/408; 424/1.1
[58] Field of Search .................... 436/501, 73, 74, 804, 436/819, 547, 548, 518; 424/1.1, 85, 88; 435/188; 530/387, 402, 405, 408

[56] References Cited
U.S. PATENT DOCUMENTS

| | | | |
|---|---|---|---|
| 4,305,922 | 12/1981 | Rhodes | 424/1.1 |
| 4,331,647 | 5/1982 | Goldenberg . | |
| 4,348,376 | 9/1982 | Goldenberg . | |
| 4,361,544 | 11/1982 | Goldenberg . | |
| 4,421,735 | 12/1983 | Haber et al. | 424/1.1 |
| 4,444,744 | 4/1984 | Goldenberg . | |
| 4,454,106 | 6/1984 | Gansow et al. . | |
| 4,460,559 | 7/1984 | Goldenberg . | |
| 4,460,561 | 7/1984 | Goldenberg . | |
| 4,472,509 | 9/1984 | Gansow et al. . | |
| 4,624,846 | 11/1986 | Goldenberg . | |
| 4,668,503 | 5/1987 | Hnatowich . | |
| 4,707,352 | 11/1987 | Stavrianpoulos . | |
| 4,732,864 | 3/1988 | Tolman . | |
| 4,732,974 | 3/1988 | Nicolotti et al. . | |
| 4,741,900 | 5/1988 | Alvarez et al. . | |
| 4,824,986 | 4/1989 | Gansow . | |

OTHER PUBLICATIONS

Chang et al., "Bifunctional Chelating Agents: Linking Radiometals to Biological Molecules," in *Applications of Nuclear and Radiochemistry*, Chapter 10, pp. 103–114.

Arano et al., "Synthesis and Evaluation of a New Bifunctional Chelating Agent for $^{99m}$Tc Labeling Proteins: p-Carboxyethylphenylglyoxal-di(N-methylthio-semicarbazone)," *Int. J. Nucl. Med. Biol.* 12:425-30 (1986).

Eckelman et al., "Radiolabeling of Antibodies," *Cancer Research* 40:3036-3042 (1980).

Holland et al., "Studies on Commercially Available $^{99}$Mo/$^{99m}$ Radionuclide Generators—I. Comparison of Five Analytical Procedures for Determination of Total Technetium in Generator Eluants," *App. Radiat. Isot.* 37:165-171 (1986).

Holland et al., "Studies on Commercially Available $^{99}$Mo/$^{99m}$Tc Radionuclide Generators—II. Operating Characteristic and Behavior of $^{99}$Mo/$^{99m}$Tc Generators," *Appl. Radiat. Isot.* 37:173-180 (1986).

*Primary Examiner*—Glennon H. Hollrah
*Assistant Examiner*—Shailendra Kumar

[57] ABSTRACT

There is disclosed a process for minimally derivatizing a targeting protein with a radionuclide such that the predominant species of derivatized targeting protein contains one radionuclide group as a single radiolabeled ligand, and whereby the binding characteristics of the targeting protein are minimally affected. There is further disclosed ligands that can chelate a metal radionuclide or bind a halogen radionuclide while providing a means for separating radiolabeled ligand from unradiolabeled ligand.

12 Claims, 8 Drawing Sheets

MINIMAL DERIVATIZATION OF PROTEINS

DESCRIPTION

1. TECHNICAL FIELD OF THE INVENTION

This invention relates to methods of minimally conjugating proteins with radionuclides so as to minimally affect the targeting and binding properties of the protein. This invention further relates to conjugated proteins with significantly retained binding and targeting properties when compared with the unconjugated protein.

2. BACKGROUND OF THE INVENTION

One of the most significant limitations of preparing radionuclide conjugates with targeting proteins, such as antibodies or antibody fragments, is the reduction of the binding specificity of the targeting protein, or the resulting loss of immune selectivity of an antibody or antibody fragment. Often, this problem is exacerbated by the use of bifunctional chelating agents with active ester groups capable of covalent binding to multiple sites, such as lysine residues on the targeting protein moiety. This results in multiple ligand binding to targeting proteins.

One approach is called the "post-formed approach" which refers to a first step of binding a ligand or a chelating group to a targeting protein, and a second step of adding the radionuclide to the conjugated protein. The result of the post-formed conjugation of a bifunctional chelating agent to a targeting protein is a plurality of bifunctional chelating agents binding to one targeting protein. In order to optimize yields of labeled proteins, ratios of one to three chelating agents per antibody are typically required. Multiple chelating agent or ligand binding is a result of a plurality of available lysine or other amino acid residues on the targeting protein that can be covalently conjugated by a ligand or a chelating group.

Bifunctional chelating groups, such as 1-benzyl substituted EDTA analogs can react with side chains of amino acids, such as tyrosine, histidine and lysine, allowing for hundreds of potential binding sites even on relatively small targeting proteins. Therefore, a sample of protein labeled with a bifunctional chelating group will contain a heterogeneous population of species labeled at different amino acid sites and different amounts of chelating groups per protein species.

Chang et al., "Bifunctional Chelating Agents: Linking Radiometals to Biological Molecules," in *Applications of Nuclear and Radiochemistry*, Chapter 10, pp. 103-14, refers to the theoretical addition of a small number of bifunctional chelating groups as determined by a statistical calculation using the Poisson distribution function. Chang et al.'s proposes this statistical solution to the problem of a heterogeneous population of conjugated proteins. Chang et al.s statistical distribution of conjugated protein species is based upon the assumption that there is an infinite number of binding sites on a protein molecule. Accordingly, Chang et al. makes the assumptions that all targeting proteins have an infinite number of binding sites and that each binding site has an equal affinity for the chelating ligand.

A further problem with the post-formed approach is binding of radionuclides directly to the protein molecule without a ligand. The field of targeting radionuclides by binding to immunospecific antibodies has focused on the labeling of antibodies preconjugated (i.e., post-formed approach) with bifunctional chelating groups, such as diethylenetriamine pentaacetic acid, EDTA (ethylenediamine tetraacetic acid) derivatives, bis-thiosemicarbazones, desferrioxamine, diamines, and diamine dimercaptide ($N_2S_2$) derivatives. The post-formed approach has an attractive simplicity which allows exchange labeling of radionuclide to chelate group derivatized antibody. However, the post-formed approach suffers from adventitious binding of metal to non-chelating agent sites on the antibody, and also from the skewed distribution of metal-antibody species formed wherein more than one metal-ligand is bound to an antibody molecule, both with a chelating ligand and through direct metal-protein binding.

Previous approaches tried to increase the activity of radionuclide at the ultimate targeting site. The means used was to increase the amount of radionuclide labeled to the targeting protein, such as a monoclonal antibody. The logic behind this approach was to load the antibody molecule with as much radionuclide as possible so as to increase the specific activity of radionuclide at the target site. For example, Goldenberg U.S. Pat. No. 4,444,744 proposes to increase the conjugation of radionuclide to antibody up to 10 iodine atoms per antibody molecule. This approach is ultimately flawed because attaching multiple ligands to antibodies has been demonstrated to adversely effect immunoreactivity. With a significant reduction of immunoreactivity of the targeting antibody, the benefit of a protein conjugate is lost, or at least significantly reduced. Alternativey, the targeting protein may be degraded by over-substitution.

The present invention was made in an effort to create radiolabeled proteins that optimally have one radionuclide ligand group per protein molecule that results in targeting (imaging, therapy, delivery) by a species which is minimally derivatized and further have all the chelating groups or ligands binding a radionuclide.

OBJECTS AND SUMMARY OF THE INVENTION

An object of the invention is to develop a process for minimally derivatizing targeting proteins. Minimal derivatization of targeting proteins relates to a heterogeneous population of radionucide-conjugated targeting proteins wherein at least 50% of the radiolabeled targeting proteins contain one radiolabeled ligand. Preferably, at least 70% of the radiolabeled targeting proteins contain one radiolabeled ligand.

It is a further object of the invention to provide a radionuclide conjugated to a targeting protein and minimal derivatization of the targeting protein with essentially no adventitious binding of radionuclide directly onto the targeting protein.

An additional object of the invention is to describe ligand systems that bind metal radionuclides and minimally derivatize targeting proteins with conjugated ligands containing a bound metal radionuclide.

It is another object of the invention to describe methods for radiohalogenating proteins by differential solubility of radiohalogenated moeity precursors and radiohalogenated moeity intermediates for protein conjugation.

The following definitions describe the terminology used herein:

Ligand: "Ligand," as used herein, refers to the chemical moiety that, binds the radionuclide. In the case of a metal radionuclide, the ligand comprises bifunctional chelating agents such as diethylenetriamine pentaacetic acid (DTPA), EDTA, bis-thiosemicarbazones, desferrioxamine, $N_2S_2$ diamide and diamine dimercaptides, .mono-amine and monoamide dimercaptides, viny iodo groups, macrocyclic polyamino (cyclam) all polyamino polyacid (TEA), hydroxamine. acids, and derivatives of each class. - A ligand can also include a radiohalogen binding agent, such as PIP (para-iodophenyl)

Targeting protein: A targeting protein is a protein, polypeptide, or fragment thereof that is capable of binding to a desired target site in vivo. The targeting protein thus serves to deliver a radionuclide to a desired target site within a human or mammalian host. The targeting protein may bind to a receptor, substrate, antigenic determinant, or other binding site on a target cell or other target site. For example, a radionuclide conjugate with a targeting protein specific for a melanoma tumor should specifically bind to tumor cells and not to non-tumor cells. Targeting proteins in this invention include, among others, antibodies and antibody fragments, monoclonal antibodies and monoclonal antibody fragments, serum proteins such as albumin, lipoproteins, and fibrinogen, fibrinoytic enzymes such as tissue plasminogen activator (t-pA), streptokinase, and urokinase, biologic response modifiers such as the interleukins, interferons and colony-stimuating factors, erythropoietin, and peptide hormones such as lutenizing hormone, growth hormone, gastrin, follicle-stimulating hormone, TSH, ACTH and others. The targeting proteins can have one or a plurality of potential binding sites for the radiolabeled ligand.

Radionuclide: The radionuclides include metal radionuclides and halogen radionuclides. Useful radionuclides include but are not limited to: Tc-99m, Re-188, Re-186, Cu-64, Cu-67, Ga-67, Ga-68, Zr-89, In-111, F-18, Br-76, Br-77, I-123, I-131, I-125, At-211, Pb-203, Pb-212, Ru-97, Rh-105, Bi-212, and Bi-206.

Radiolabeled Ligand: A radiolabeled ligand comprises a radionuclide and a ligand. The ligand may be a chelating agent for metal radionuclides or an organic group, such as para-iodophenyl, or PIP, for radiohalogens and other covalent binding radionuclide elements.

The present invention provides, in one aspect, a process for conjugating a targeting protein with a radionuclide. The predominant species of radiolabeled targeting protein has one radiolabeled ligand per protein molecule. The process comprises:

binding a radionuclide with a ligand to form a radiolabeled ligand and then conjugating the radiolabeled ligand to a targeting protein in an appropriate molar ratio so as to minimally effect the binding characteristics of the targeting protein The binding reaction or the conjugating reaction provides a means for separating the radiolabeled ligand from the unradiolabeled ligand.

In another aspect, the invention provides a conjugated targeting protein wherein the predominant species of conjugated targeting protein has only one radionuclide bound to it through a carrier molecule, such as a ligand. In yet another aspect, the invention comprises a conjugated targeting protein conjugated by the inventive process.

This invention further comprises bifunctional chelating ligands and radiohalogenation systems that provide a means for separating radiolabeled ligand from unradiolabeled ligand.

DESCRIPTION OF THE DRAWINGS

FIG. 3 shows decreasing immunoreactivity, as measured by in vitro cell-binding radioactivity, with increasing molar ratios.

DETAILED DESCRIPTION OF THE INVENTION

Figure 1A:
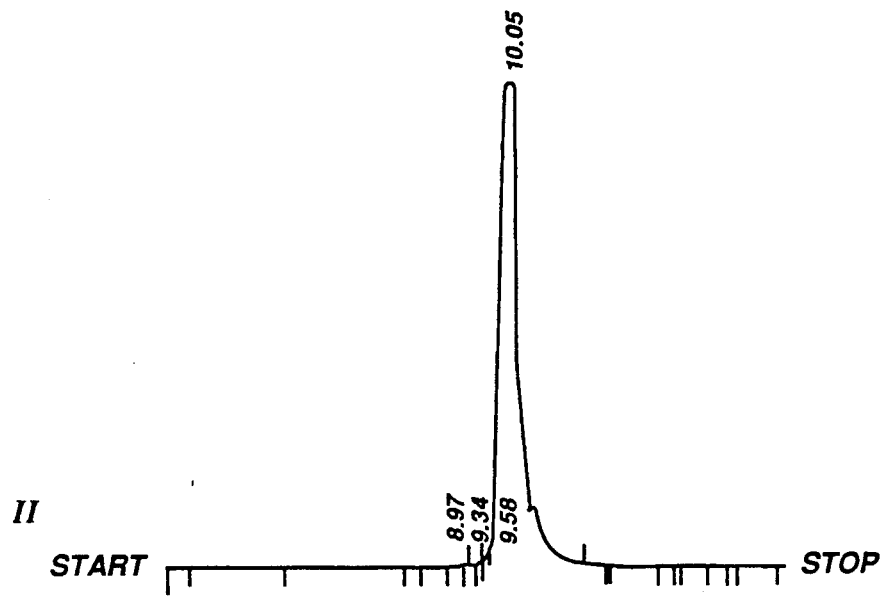
FIG. 1 is a high pressure liquid chromatogram (HPLC) of a conjugated antibody with the radionuclide Tc-99m offered with no carrier added (lower tracing) and with Tc-99m bound to ligand and conjugated at a molar ratio of 1.4 moles of bound (to a ligand) radionuclide to 1 mole of antibody (targeting protein).

The present invention relates to a process for producing radionuclide-abeled targeting proteins for in vivo diagnostic or therapeutic purposes. The conjugated targeting proteins are heterogeneous with one or a plurality of radionuclides bound to a targeting protein, but wherein the predominant species has one radionucide moiety bound through a ligand to the targeting protein. In yet another aspect, the invention describes specific ligands useful for binding, with appropriate molar ratios, to achieve the minimally derivatized, one radionuclide moiety per targeting protein molecule. The inventive process utilizes a "preformed" approach whereby the radionuclide is joined with the ligand to form the radiolabeled ligand, which subsequently is attached to a targeting protein. The inventive process also has a means for separating radiolabeled ligand from unradiolabeled ligand. This process is in contrast with the "post-formed" approach as described in Goldenberg U.S. Pat. No. 4,444,744, wherein the ligand is conjugated to the protein and the radionuclide is later added to the conjugated protein. The preformed approach avoids the problem of adventitious binding of radionuclide directly to the protein. When radionuclide is bound directly to the targeting protein, the radionuclide release kinetics cannot be controlled. The preformed approach does not address the problem of conjugation of an unradiolabeled ligand to the targeting protein. The inventive process and the novel ligands disclosed herein provide a means for separating radiolabeled ligand from unradiolabeled ligand when the label moiety is being "preformed." Thus, the conjugation reaction predominantly binds the radiolabeled ligand to a targeting protein. Certain embodiments of the present invention provide methods wherein essentially all (i.e., approximately 95%) of the ligand bound to the targeting protein is radio-labeled. Preferably, the binding of radionuclide to ligand and means for separating radiolabeled ligand from unradiolabeled ligand is completed within about four hours because some radionuclides, such as Tc-99m, have short half-lives. Most preferably, the inventive process is completed within about four hours.

The present invention also relates to a mixture of species of radionuclide-labeled (radiolabeled ligand) targeting proteins wherein the predominant radiolabeled species is a single radionuclide-labeled ligand moiety conjugated to the targeting protein. The term "predominant," as used herein, means the single-labeled targeting protein species is at least 50% of all radionuclide-labeled targeted protein molecules when the targeting protein molecule has a plurality of ligand conjugation sites. This result achieves the goal of minimal derivatization. Preferably, the predominant single-radiolabeled species comprises at least 70% of the conjugated targeting proteins. It is generally advantageous to provide for a minimal derivatization of the targeting protein with one radionuclide-bound ligand per targeting protein. This results in maximal targeting protein reactivity and maximal homogeneity of the reagent, when the targeting protein has a plurality of ligand binding sites.

For example, a radionuclide, such as Tc-99m, chelated to an $N_2S_2$ bifunctional chelating ligand with an active ester protein conjugation group can bind to a lysine residue of a protein. Thus the Tc-99m - $N_2S_2$ radiolabeled ligand can bind to a plurality of sites on a targeting protein, limited only by the number of available lysine residues in the protein.

Conversely, if the Tc-99m - $N_2S_2$ is bound to an oligopeptide, such as D-phenylalanine-L-proline-L-arginine-chloromethyl ketone (which is abbreviated as D-Phe-Pro-ArgCH$_2$Cl and sold as "PPACK" by Calbiochem as a thrombin inhibitor), the PPACK moiety can specifically bind to the fibrinolytic active site on the t-PA enzyme. This thrombin inhibitor was described by Kettner et al., *Thrombosis Research* 14:969-73. As it is believed there is only one fibrinolytic active site per t-PA molecule, then only one ligand complex can be bound to a t-PA targeting protein. t-PA retains its targeting function even with PPACK specifically bound because the fibrin binding site remains available. Therefore, the compound designated as "PPACK" can be used as a linker for the specific binding of a label moiety to the portion of the t-PA enzyme responsible for catalyzing the conversion of plasminogen to plasmin. U. S. Pat. Application No. 01,329, filed on Sept. 25, 1987 and incorporated by reference herein, describes the attachment of a radionucide complexed within a ligand to this tripeptide linking group. When the tripeptide linking group binds to t-PA, the result is both a stable and covalent attachment of the radionuclide to the targeting protein and a reduction of the plasminogen-activating activity of the enzyme. The fibrin-binding property of t-PA is retained.

A single-ligand binding site targeting protein such as t-PA can always have no more than one ligand bound to the targeting protein for ligands specific to the one binding site, such as PPACK. The present inventive process provides for a means for separating radiolabeled ligand from unradiolabeled ligand. Therefore, a preformed process wherein the radiolabeled ligand is separated from the unradiolabeled ligand before binding to a linker, such as PPACK, that can bind to only one targeting protein binding site, will provide a radiolabeled targeting protein, such as t-PA, wherein substantially all of the conjugated targeting proteins will be radiolabeled.

In order to achieve minimal derivatization of the targeting protein using the preformed approach, the process by which the radiolabeled protein is produced should include a means for selectively conjugating radiolabeled ligands (as opposed to unradiolabeled ligands) to the targeting protein. The number of radiolabeled ligands that bind to the protein also should be controlled during the radiolabeling reaction to achieve sufficient radiolabeling for the intended diagnostic or therapeutic use without decreasing the targeting property of the protein by attaching too many ligands thereto.

In accordance with the present invention, a process for conjugating a targeting protein with a radiolabeled labeled ligand comprises binding a radionuclide with a ligand to produce a radiolabeled ligand wherein the binding reaction provides a means for separating the radiolabeled ligand from the unradiolabeled ligands. The radiolabeled ligands are conjugated to a targeting protein such that the predominant species of conjugated targeting protein molecule is a targeting protein having one radiolabeled ligand attached thereto. The conjugated (i.e., radiolabeled) targeting protein thus is minimally derivatized.

The process of the invention for conjugating a targeting protein with a radiolabeled ligand provides a method for reducing the incidence of binding of unradiolabeled ligands to targeting protein molecules. Binding of unradiolabeled ligands is undesirable because such binding generally adversely affects the targeting properties of the protein (especially when multiple ligands are attached thereto) without providing the benefit of a radiolabel.

In one embodiment of the invention, the means for separating the radiolabeled ligands from the unradiolabeled ligands is a change in a physical property of the radiolabeled ligands. This change occurs during the binding reaction (i.e., the radiolabeling reaction) and may be, for example, a change in the solubility (e.g., lipophilicity or water solubility) or charge of the ligand molecule, or combinations thereof.

Such a change in the physical properties of the ligand may occur when a particular substituent or chemical group on the ligand is displaced, hydrolyzed, or otherwise removed from the ligand molecule during the radiolabeling reaction, wherein loss of this substituent changes a physical property of the ligand and occurs only in ligands that bind a radionuclide. Thus, such a chemical group susceptible to hydrolysis or displacement by the radiolabeling of a particular ligand may be attached to the ligand. The chemical group may be attached to a donor atom in a chelating compound, such that the group is displaced when a bond between the donor atom and the radionuclide forms during the radiolabeling reaction.

The resulting difference in the physical properties of the radioabeled and unradiolabeled ligands permits separation using standard methods, such as chromatography columns that separate molecules having different charges or solubility. The radiolabeled ligands then are conjugated to a targeting protein.

Alternatively, the difference in physical properties may be used to selectively conjugate the radiolabeled ligand to the targeting protein, even when both the radiolabeled and unradiolabeled ligands are present in the conjugation reaction mixture. A very changeable physical property is that of aqueous solubility. Thus, if highly lipophilic groups are present on the non-radiolabeled ligand but are not present on the radiolabeled ligand, a large partitioning can occur to have primarily the radiolabeled ligand available for reaction with the protein. Another alternative separation method of radiolabeled ligand from unradiolabeled ligand is differential solubility due to a change in charge. Thus, a neutral ligand may require organic solvent for chelation. The radiolabeled product may be charged, and thus have increased water solubility. Addition of water for protein conjugation effectively reduces unradiolabeled ligand concentration.

Thus, a higher percentage of a particular water-soluble, radiolabeled ligand is expected to react with a targeting protein in an aqueous medium than the substantially less water-soluble, unradiolabeled ligand. Protein conjugation reactions generally are conducted in aqueous reaction mixtures because proteins may be denatured or otherwise adversely affected by organic solvents. The separation of the radiolabeled and unradiolabeled ligands thus occurs by selective reaction of the abeled ligands with the protein, followed by purification of the resulting radiolabeled (i.e., conjugated) targeting protein from the reaction mixture using conventional techniques (e.g., chromatography).

An example of partition separation is the use of the very water-insoluble tri-N-butylstannyl moiety as a reactive intermediate in radiohalogenations, yielding a reasonably soluble radiohalogenated ligand upon labeling with halogen radionuclides and subsequent dilution in the aqueous protein conjugation reaction medium. The use of ligands comprising tri-N-butylstanyl groups as intermediates in radiohalogenation procedures is described, for example, in European Patent Application Publication No. 203,764, entitled "Radiohalogenated Small molecules for Protein Labeling." One such radiohalogenation reaction is depicted as follows, in which a ligand comprising a phenyl ring bearing a protein conjugation group is radiohalogenated at the para position:

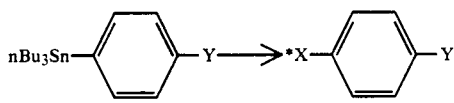

wherein Y represents a protein conjugation group (i.e., a functional group reactive with a protein) or a precursor thereof, and *X represents a radiohalogen (e.g., $211_{At}$, $131_I$, $125_I$, $123_I$, or $76_{Br}$, among others).

A second method of obtaining a solubility difference is to use water-insoluble salts of the non-radiolabeled ligand, which upon radiolabeling produce a more water-soluble radiolabeled ligand. An example of this is found in the use of the extremely insoluble pentafluorosilicate salts in radiohalogenations, whereby the reaction with the halogen radionuclide converts the salt to the halide. One such reaction is depicted as follows:

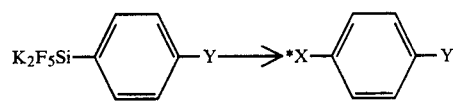

wherein Y is a protein conjugation group or a precursor thereof and *X represents a radiohalogen.

Another means for separating radiolabeled ligands from unradiolabeled ligands involves attaching the unradiolabeled ligand to an insoluble support material. The attachment of the unradiolabeled ligand to the support is such that the radiolabeling reaction causes release of radiolabeled ligands (but not the unradiolabeled ligands) from the insoluble support. Thus, the radiolabeled ligands are separated from the unradiolabeled ligands and are then conjugated to a targeting protein The stoichiometry of the radiolabeled ligand is limited to the amount of radionuclide present.

The insoluble support material may be any suitable support that does not interfere with the radiolabeling reaction. Materials such as agarose, sepharose, cellulose, latex, silica, polymers, and derivatives thereof may be used. Various support materials bearing functional groups that will react with a group on a ligand to bind the ligand thereto are known. The support may be placed into a column after attaching the unradiolabeled ligand thereto. Alternatively, separation of the insoluble material (e.g., in the form of beads) having the unradiolabeled ligand attached thereto may be effected by centrifugation after the radio-labeling reaction.

In one embodiment of the invention, ligands which are chelating compounds comprising at least one sulfur donor atom are attached to a solid support. The donor atoms are atoms that form bonds to a radionuclide metal during the radiolabeling reaction, thereby forming the corresponding radionuclide metal chelate. A sulfur-protecting group attached to a sulfur donor atom comprises a functional group that will react with a solid (insoluble) support material, thereby attaching the unradiolabeled ligand to the support. When a bond forms between a radionuclide and the sulfur donor atom during radiolabeling, the bond between the sulfur donor atom and the sulfur-protect group is cleaved, thereby releasing the radionuclide chelate from the insoluble support. One example is a diamide dimercaptide ($N_2S_2$) chelating compound represented by the following formula:

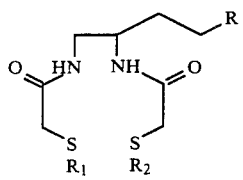

wherein R represents a protein conjugation group (described below) and $R_1$ and $R_2$ represent sulfur-protecting groups wherein at least one of $R_1$ and $R_2$ comprises a functional group that will react with an insoluble support to attach the chelating compound to the support.

In one embodiment of the invention, $R_1$ and $R_2$ are represented by the formula:

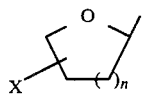

wherein X is a group reactive with an insoluble support and n is an integer of from about 1 to about 3. Preferably, X is not attached to a carbon atom that is alpha to the oxygen atom. $R_2$ may be the same as or different from $R_1$.

The X group will vary according to the particular insoluble support to be used. Suitable X groups include, but are not limited, those of the formula: —$(CH_2)_n$—Q, wherein n is an integer from 1 to about 6 and Q is an active ester, other leaving group, or a Michael-type acceptor, such as maleimide. For example, certain insoluble support materials comprise free amine groups, and an X group, such as an active ester, which is reactive with amines, therefore is chosen for use. Such support materials include Sepharose-4B columns, among many others.

In an alternative embodiment of the invention, $R_1$ is a substituted benzyl group, wherein the substituent is of the formula: —$(CH_2)_n$—X, wherein n is an integer from 1 to about 4 and X is a group reactive with an insoluble support, as described above. $R_2$ is of the formula: —CO alkyl, wherein the alkyl group is methyl or substituted methyl.

When a particular R group would react with the solid support to be used, the ligand may comprise precursor of the desired R group. The R group may be generated from the precursor, using standard techniques, after the ligand is attached to the solid support. In one embodiment of the invention, the ligand may comprise a -COOH group at the R position. The carboxylic acid group is a precursor of an active ester, which would react with a solid support material containing free amine groups (e.g., Sepharose-4B). The ligand is reacted with the insoluble support material, whereupon the "X" group of substituent $R_1$ or $R_2$ reacts with the solid support to bind the chelating compound thereto. An active ester group then is produced from the —COOH group by reaction with the appropriate alcohol, using a standard mixed anhydride reaction, for example.

After the ligand is attached to the insoluble support, radiolabeling with a suitable radionuclide of interest (e.g., $^{99m}Tc$, $^{188}Re$, or $^{186}Re$) is conducted using conventional procedures, as described below. The radiolabeled ligands are released from the support to yield the resulting radionuclide metal chelate which is depicted by the following formula:

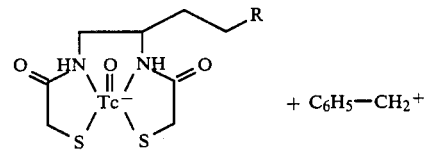

wherein other radionuclides may be used in place of $^{99m}Tc$. The radiolabeled ligands thus separated from unradiolabeled ligands then are conjugated to a targeting protein Another example of release of a radiolabeled ligand from a solid support material is shown as follows

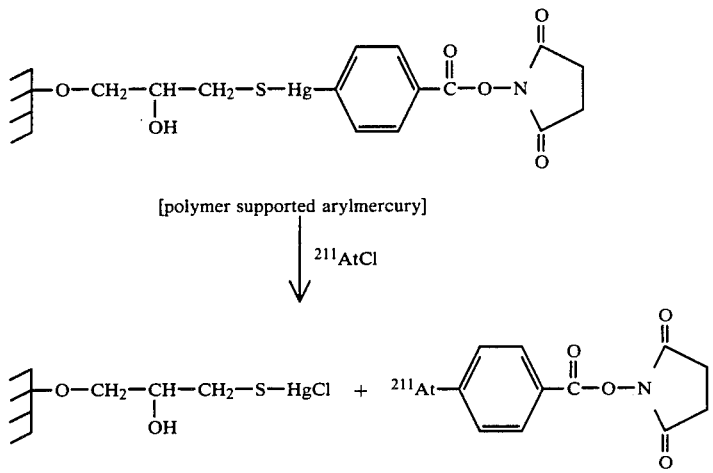

wherein other protein conjugation groups may be used in place of the succinimidyl ester group.

An alternative means for separating radiolabeled ligands from unradiolabeled ligands involves the use of ligands which do not comprise protein conjugation groups until radiolabeled. A protein conjugation group is generated on such ligands during the radiolabeling reaction.

Examples of such compounds are Compounds 1 and 2, which have a modified t-butyl group as a sulfur-protecting group, which can be converted to α,β-unsaturated compound during the labeling process.

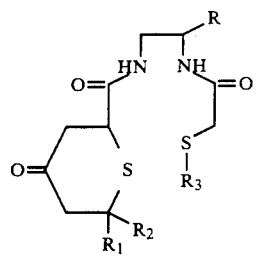 1

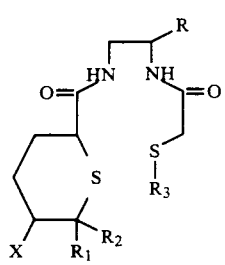 2 wherein R is a side chain containing polar groups or transfer groups; $R_1$ is H or $CH_3$; $R_2$ is $CH_3$; $R_3$ is a conventional sulfur-protecting group; and X is an electron withdrawing group, such as, but not limited to, COOEt, CN, and $NO_2$.

Examples of R groups include, but are not limited to $(CH_2)_{1-5}-SO_3H$, $CH_2$-gluconate, hydroxy acids, and amino hydroxy acids. The polar groups serve to enhance the water solubility of the ligands. The gluconate, hydroxy acid, and amino hydroxy acid components of the last three polar groups are "transfer agents." A radionuclide metal is quickly but temporarily bound through relatively labile bonds to these transfer agents. The radionuclide subsequently is transferred (e.g., by heating) to the site at which the four bonds to the four donor atoms (two sulfur and two nitrogen atoms) form to produce the final chelate. In the case of Compounds 1 or 2, the radionuclide binding can be done at a pH of about 6.5 to about 7.0 to generate the carbonium ions (Compounds 3 and 5, respectively). Compounds 4 and 6, respectively, are generated in situ and will react with a targeting protein to form a covalent bond. The highly reactive protein conjugation group (an activated double bond) produced in Compounds 4 and 6 will react with a targeting protein containing free sulfhydryl groups. Conventional methods may be used to produce free sulfhydryl groups on antibodies, for example.

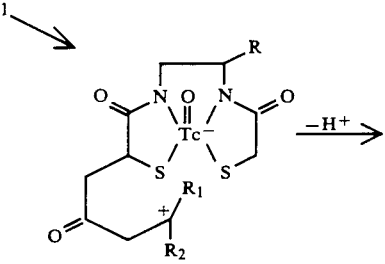 3

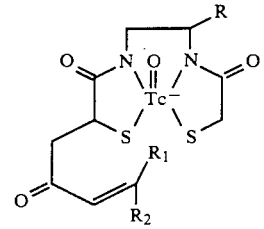 4

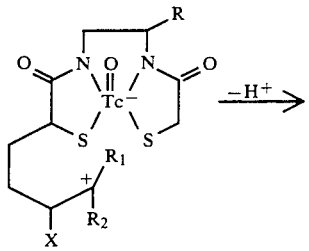 5

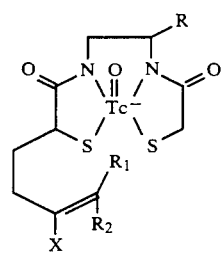 6

The unradiolabeled ligands cannot react with proteins.

Further, the same modified t-butyl sulfur-protecting groups can be used with an $N_3S$ and ligand system containing at least one amine group, as in Compounds 7 and 8 below.

7

8 wherein $R_1$ and $R_2$ are as described above for Compounds 1 and 2, and $R_4$ represents any two suitable substituents.

The various ligands which may be used are radiolabeled using conventional procedures. When the ligand is a chelating compound, the chelating compounds are radiolabeled with an appropriate radionuclide tc produce the corresponding chelate Conventional procedures are used for radiolabeling the chelating compounds. For example, pertechnetate ($^{99m}TcO_4-$) or perrhenate ($^{186}$ or $^{188}ReO_4-$) are generally contacted with a chelating compound in the presence of a reducing agent (e.g., a ferrous or stannous salt or dlLhionite) to effect reduction of the radionuclide to an oxidation state at which chelation can occur. Alternatively, the pertechnetate or perrhenate may be reduced in the presence of a relatively labile transfer agent, such as gluconic acid or citric acid, to form intermediate complexes ($^{99m}Tc$-gluconate or $^{186}Re$-citrate). When the intermediate complexes are contacted with the chelating compounds under appropriate reaction conditions, the radionuclide metal is transferred to the chelating compound, thereby producing a radionuclide metal chelate.

Procedures for attaching radiohalogens to a ligand are described in European Patent Application publication No. 203,764, which reates to para-iodophenyl ligands and ligands labeled with radiohalogens other than iodine.

Once the radiolabeled ligand is obtained, it can be conjugated to the targeting protein either directly such as a through an active ester moiety on the ligand, or through a linking group. Suitable protein conjugation procedures are described in European Patent Application publication No. 188,256. In general, the ligand and the targeting protein are combined in a buffered aqueous solution under physiologicaly acceptable conditions of temperature and pH.

The conjugation process is conducted by reacting a relatively low molar ratio of radiolabeled ligand to targeting protein so as to produce a predominant species of radiolabeled protein having a single radiolabeled ligand attached to each targeting protein molecule. A molar ratio of about 1:1 may be used in some cases, but ratios in which the amount of radiolabeled ligand molecules offered per antibody molecule is less than one are generally preferred. The various types of targeting proteins may vary in the degree to which conjugation of ligands affects the targeting ability of the protein. Based upon a targeting protein with a plurality of ligand binding sites, and a Poisson probability distribution, a molar ratio from about 0.01 to about 0.5 radiolabeled ligand to targeting protein should provide predominantly a minimally derivatized targeting protein, wherein the predominant species of conjugated targeting protein is a targeting protein molecule having one radiolabeled ligand per targeting protein molecule, so as to minimally affect its binding-targeting characteristics. Preferably, the molar ratio should be approximately 0.3, which, according to the Poisson distribution, will have 74.1% of the radiolabeled targeting proteins with one radiolabeled ligand, 22.2% with two radiolateled ligands, 3.3% with three radiolabeled ligands, and 0.4% with four or more radiolabeled ligands of the targeting proteins with any bound ligands. If, for example, a molar ratio of 3:1 is used, Poisson distribution results indicate that only 5% of the targeting proteins with a bound ligand will be minimally derivatized with only one bound ligand per targeting protein, whereas 57.7% will have four or more bound ligands and compromised immunoreactivity.

The proteins to be conjugated to radiolabeled ligands generally are targeting proteins. The term "targeting protein," as used herein, refers to proteins which bind to a desired target site in vivo, as described above.

These proteins may be modified (e.g., to produce variants and fragments of the proteins) as long as the desired biological property (i.e., the ability to bind to the target site) is retained. The proteins may be modified by using various genetic engineering or protein engineering techniques.

Antibodies may be used as targeting proteins. The antibodies may be polyclonal or monoclonal, with monoclonal antibodies (MAbs) specific for target cells being preferred. A number of monoclonal antibodies that bind to a specific type of cell have been developed, including MAbs specific for tumor-associated antigens in humans. Among the many such MAbs that may be used are anti-TAC, or other interleukin-2 receptor antibodies; 9.2.27 and NR-ML-05 to the 250 kilodalton human melanomaassociated proteoglycan; NR-LU-10 to 37-40 kilodalton pancarcinoma glycoprotein; and OVB3 to an as yet unidentified tumor-associated antigen. Antibodies derived through genetic engineering or protein engineering may be employed as well. The antibody employed in the present invention may be an intact molecule, a fragment thereof, or a functional equivalent thereof. Examples of antibody fragments are $F(ab')_2$, $Fab'$, and $F_v$ fragments, which may be produced by conventional methods or by genetic or protein engineering.

The procedure for attaching a radiolabeled ligand to a targeting protein, such as an antibody, will vary according to the chemical structure of the ligand. Antibodies are proteins that contain a variety of functional groups; e.g., carboxylic acid (COOH) or free amine ($-NH_2$) groups, which are available for reaction with a suitable functional group (i.e., protein conjugation group) on a ligand molecule to bind the ligand thereto. Alternatively, the protein and/or ligand may be derivatized to expose or attach additional reactive functional groups. The derivatization may involve attachment of any of a number of linker molecules, such as those available from Pierce Chemical Company, Rockford, Illinois. (See the *Pierce* 1986–87 General Cataloq, pp. 313–354.) Alternatively, derivatization may involve chemical treatment of an antibody. procedures for generation of free sulfhydryl groups on antibodies or antibody fragments (e.g., by reduction of disulfides to generate thiol groups) are known. (See U.S. Pat. No. 4,659,839.) The free thiol groups may, for example, be reacted with an activated double bond (e.g., the double bond of a maleimide group on a linker) to produce a thioether bond. Many procedures and linker molecules for attachment of various compounds to proteins such as antibodies are known.

As used herein, the term "protein conjugation group" refers to a functional group that will react with a protein. A protein conjugation group on a ligand will react with a group on a protein under physiologically acceptable conditions, thereby binding the ligand to the protein. Examples of suitable protein conjugation groups include, but are not limited to, imide esters, alkyl imide esters, succinimide esters, acylsuccinimides, imidate esters, phenolic esters, substituted phenolic esters, tetrafluorophenyl esters, anhydrides, isothiocyanates, amines, hydrazines, hydrazides, alkyl halides, and Michael-type acceptors, such as maleimides.

Minimally derivatized targeting protein molecules (one radiolabeled ligand attached thereto) are the predominant species in the population of conjugated (i.e., radio-labeled) protein molecules. Minimally derivatized proteins generally will not be the predominant species in the conjugation reaction mixture as a whole since a significant portion of all the targeting protein molecules will not have any radiolabeled ligands bound thereto. Advantageously, the ratio of radiolabeled ligand to protein in the conjugation reaction mixture is chosen to minimize the number of protein molecules having more than one radio-labeled ligand bound. This reduces the number of radio-labeled targeting molecules with diminished targeting properties by virtue of multiple radionuclide binding. The effect, however, of low molar ratios of radiolabeled ligands to targeting protein during the conjugation reaction is that a significant percentage of targeting proteins will not be radiolabeled. The presence of non-radiolabeled or unconjugated targeting proteins will not adversely affect the diagnostic or therapeutic uses of the radiolabeled targeting protein. Preferably, the radionuclide has sufficiently high specific activity to allow therapeutic or diagnostic use of the radiolabeled protein conjugate.

The following examples illustrate the practice of the invention a variety of the radionuclides. The examples are offered by way of illustration and not limitation.

EXAMPLE 1

This example illustrates how the minimal derivatization process results in a more homogeneous distribution of radionucide conjugated monoclonal antibodies. Tc-$^{99m}$ has a specific activity of 2 millicurie per pmole from the generator source used. Tc-$^{99m}$ rapidly decays to Tc-$^{99m}$ with a 6 hour half life. Therefore, eluants of Tc-99m will always contain the $\beta$ emitter Tc-99, with its approximately 200,000 year half-life. The amount of Tc-99 present depends upon the length of time between elutions of the Molybdenum-99/Tc-99m generator, as Tc-99m is decaying to Tc-99 while on the generator column. Holland et al., "Studies on Commercially Available $^{99}$Mo./$^{99m}$Tc Generators", Appl. Radiat. Isot. 37:173-80, 1986, has determined the amount of technetium present in generator eluates. The concentrations resulting from normal elution conditions measured ranged up to $1.0 \times 10^{-5}$ M, with greater than 90% of the generator eluates having concentrations of $10^{-6}$ to $10^{-7}$ M (Holland et al., "Studies on Commercially Available $^{99}$Mo/$^{99m}$Tc Generators I. Comparison of Five Analytical Procedures for Determination of Total Technetium in Generator Eluates," *App. Radiat. Isol.* 37:65-70, 1986.

This example uses the upper limit of 10-6 eluate concentration and 1 ml of eluate, or 1.0 nmole of Tc-99m and Tc-99. The targeting protein is an antibody fragment (Fab) with a molecular weight of 50,000 daltons. 2.5 mg of Fab fragment is used, or 50 nmoles.

This example examines varying molar ratios of Tc to antibody. The Tc eluate is bound to a diamide dimercaptide ($N_2S_2$) ligand to form a label moiety with a means for separating the radiolabeled ligand from the unradiolabeled ligand. The radiolabeled ligand is conjugated to the Fab fragment at different molar ratios to form the minimally derivatized protein conjugate.

The labeled conjugate is analyzed by isoelectric focusing electrophoresis (IEF) for an analysis of the charge alteration resulting from the protein conjugation reaction.

Figure 6:
FIG. 6 shows the isoelectric focusing of radio-labeled antibody at different molar ratios of radiolabeled ligand to antibody.
Figures 7A, 7B:
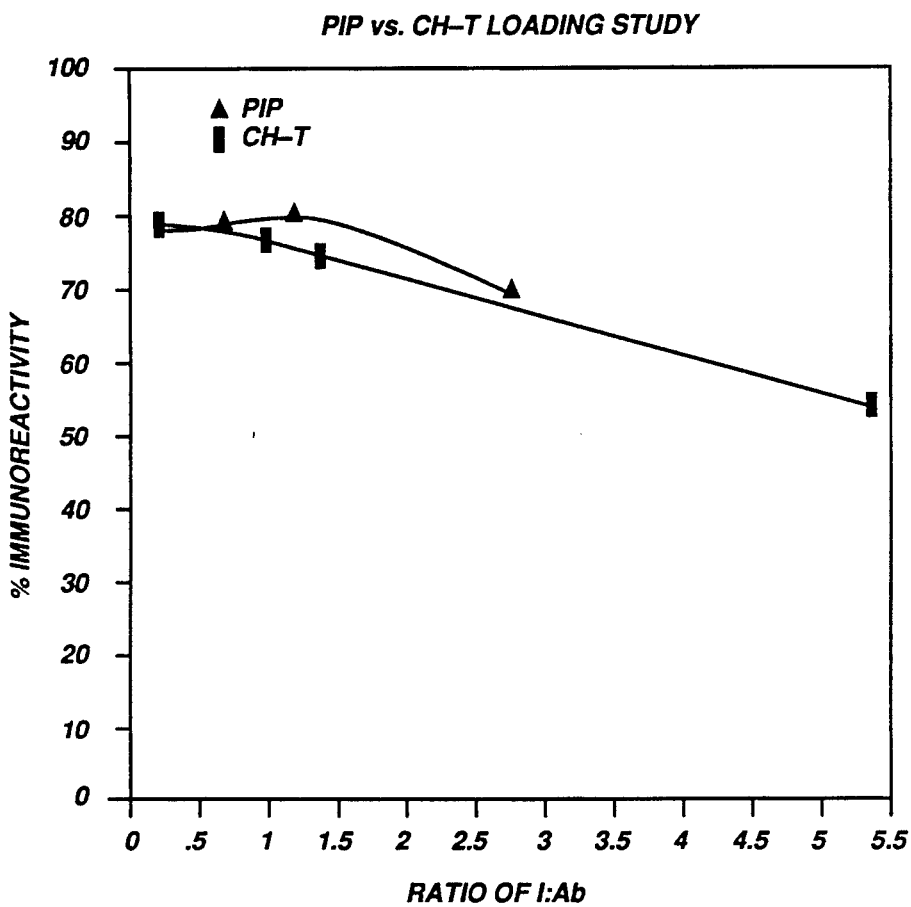
FIG. 7 is a graph of Table I comparing the immunoreactivity of PIP (para-odophenyl) and CH-T (chloramine-T) when conjugated to the antibody targeting protein NR-ML-05 at four molar ratios of radiolabeled ligand to targeting protein.
Figure 8:
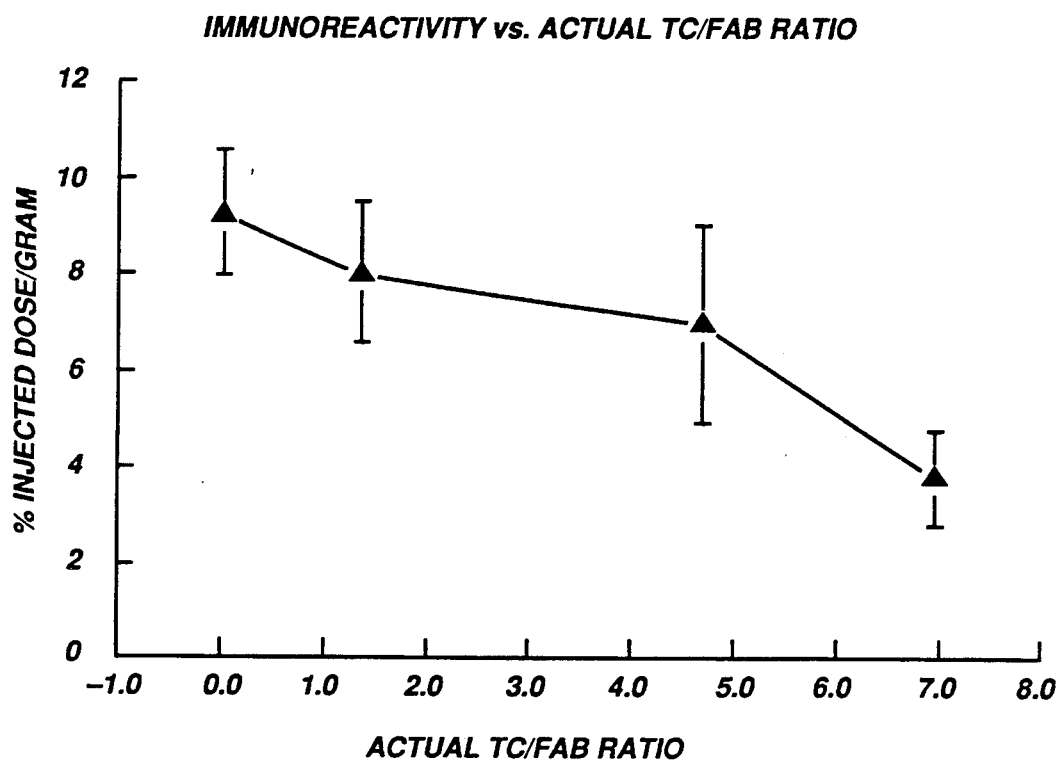
FIG. 8 compares the immunoreactivity of a monoclonal antibody as percentage of injected dose of the radionuclide (Tc-99m) per gram of target tumor tissue as a function of the molar ratio of radiolabeled ligand to targeting protein (monoclonal antibody fragment). The radionuclide is Tc-99m.

The alteration of charge as shown by isoelectric focusing (FIG. 6) shows the extent of protein derivatization. For example, autoradiography shows a shift of the two bands in the antibody as seen by Coomassie blue staining. A lack of shift of the stain at no carrier TC-99 added is consistent with the low (1:50) Tc:antibody fragment ratio. At Tc-99 carrier added levels, the autoradiographic bands and stain coincide as expected when the ratios of Tc to antibody are comparable. As the Tc-99 carrier is increased and the ratio of Tc to antibody fragment increases, both the bands shift more anionic and more bands result from the species resulting from different degrees of substitution.

Figure 1B:
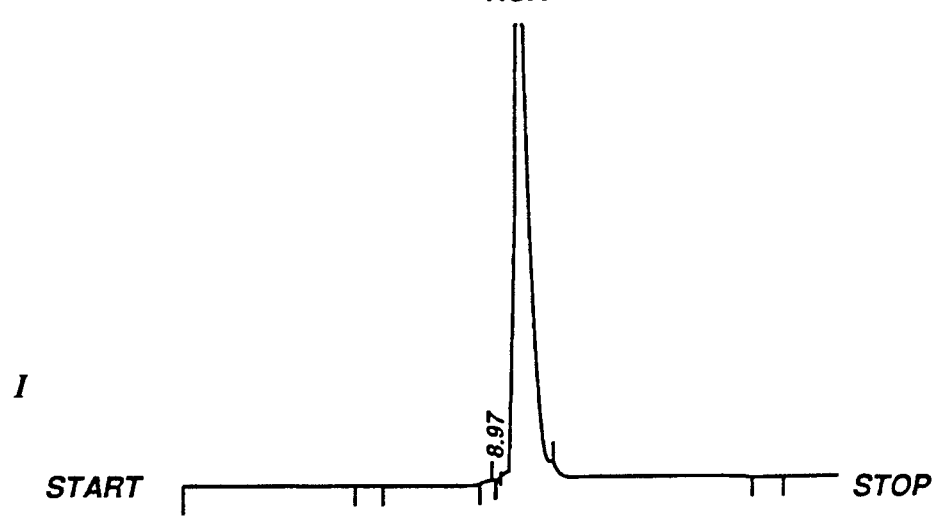
Figure 2A:
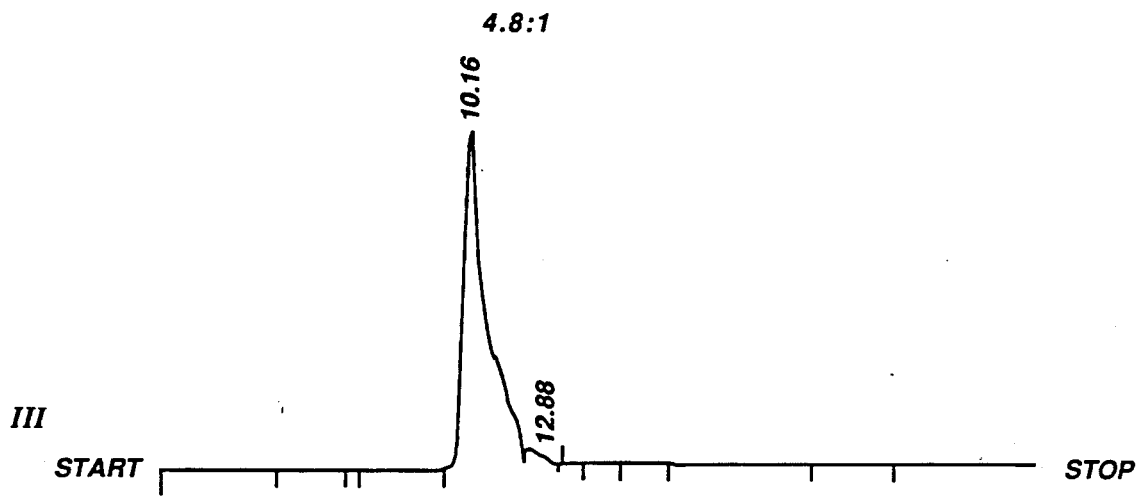
FIG. 2 is the HPLC results of a conjugated antibody, conjugated by the inventive process with To-99m as the radionuclide at the molar ratios of 4.8:1 (top) and 7.4:1 (bottom). Note that the HPLC peaks are increasingly skewed as the molar ratios are increased in FIGS. 1 and 2.
Figure 2B:
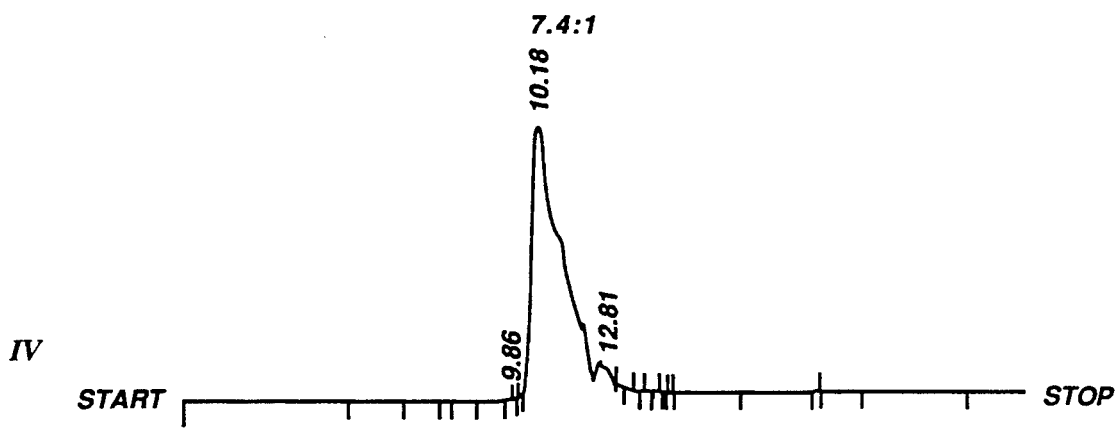

HPLC gel filtration of the conjugated monoclonal antibody fragment of NL-ML-05 Fab with the label moiety moiety Tc-N2S2 at a 1.4:1 molar ratio was essentially unchanged from the "no carrier added" (NCA) preparation. See FIG. 1. At higher loading levels, in FIG. 2, peak broadening was observed. This is consistent with multiple species from the higher molar ratios.

EXAMPLE 2

Figure 3:
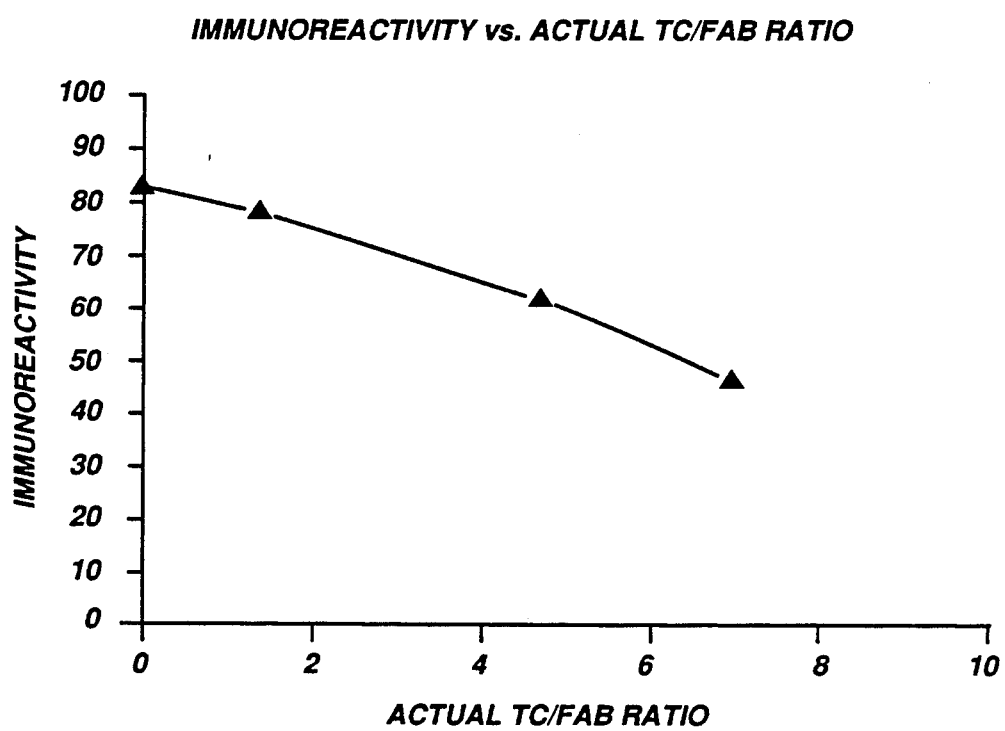
FIG. 3 is a graph of the immunoreactivity of a conjugated antibody, conjugated with the radionuclide Tc-99m and produced by the inventive process using molar ratios of bound radionuclide to targeting protein of up to 7.0:1.

This example illustrates how the minimal derivatization process results in minimal inhibition of antibody immunoreactivity. Immunoreactivity was assessed by in vitro cell binding using Tc-99m radioactivity binding to melanoma cells in an antigen excess assay according to the procedure in Lindmo et al., *J. Immunol Meth.* 72:77-89, 1984. FIG. 3 shows the results of four molar ratios to Tc-$N_2S_2$ to antibody fragment and the relative immunoreactivity of the resulting conjugates as expressed in percent Tc-99m bound to cels. There was a decrease in immunoreactivity with increasing ratio of the Tc-$N_2S_2$ label moiety to antibody fragment molar ratio.

EXAMPLE 3

Figure 4A:
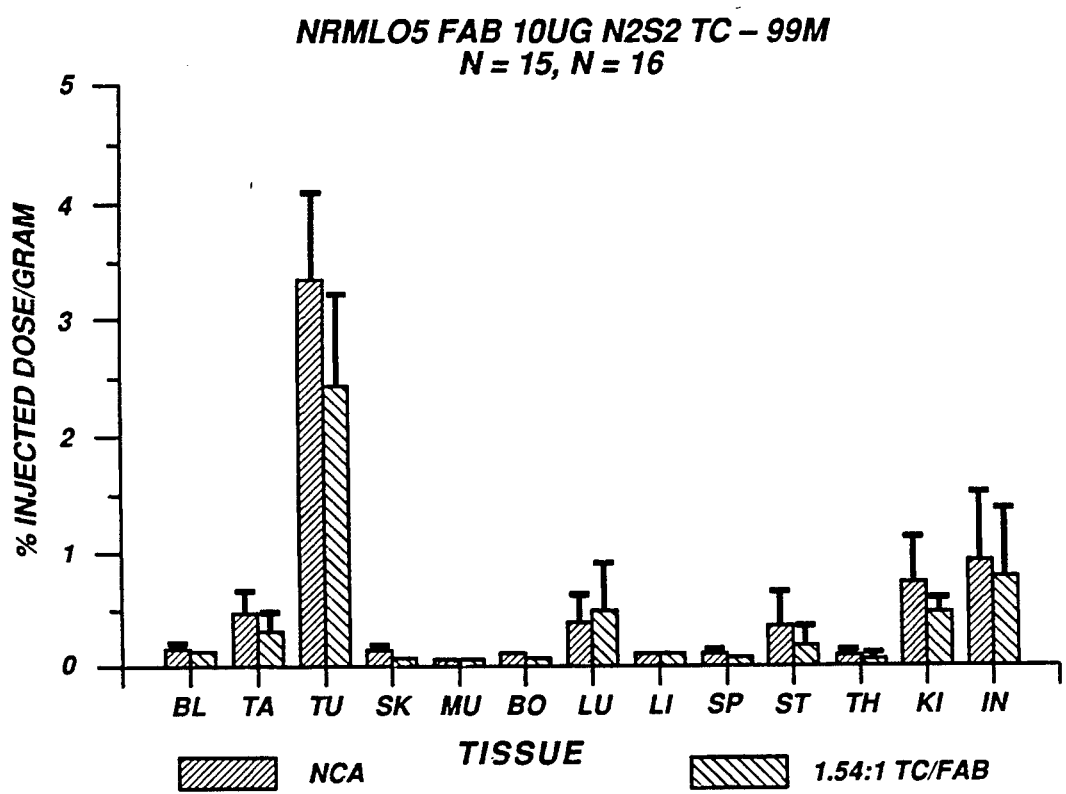
FIG. 4 shows the tissue and tumor breakdown of nude mice bearing A375 melanoma xenografts for radioactivity. The nude mice were injected with a protein conjugate comprising a NR-ML-05 monoclonal antibody fragment conjugated with Tc-99m in an $N_2S_2$ ligand at different molar ratios. A 10 microgram dose was injected and the tissue and tumor distribution determined at 20 hours post-injection. The distribution symbols are: BI,-blood; TA-tail; TU-tumor; SK-skin; MU-muscle; BO-bone; LU-lung; LI-liver; Sp-spleen; ST-stomach; TH-thryoid; KI-kidney; and IN-intestine.
Figure 4B:
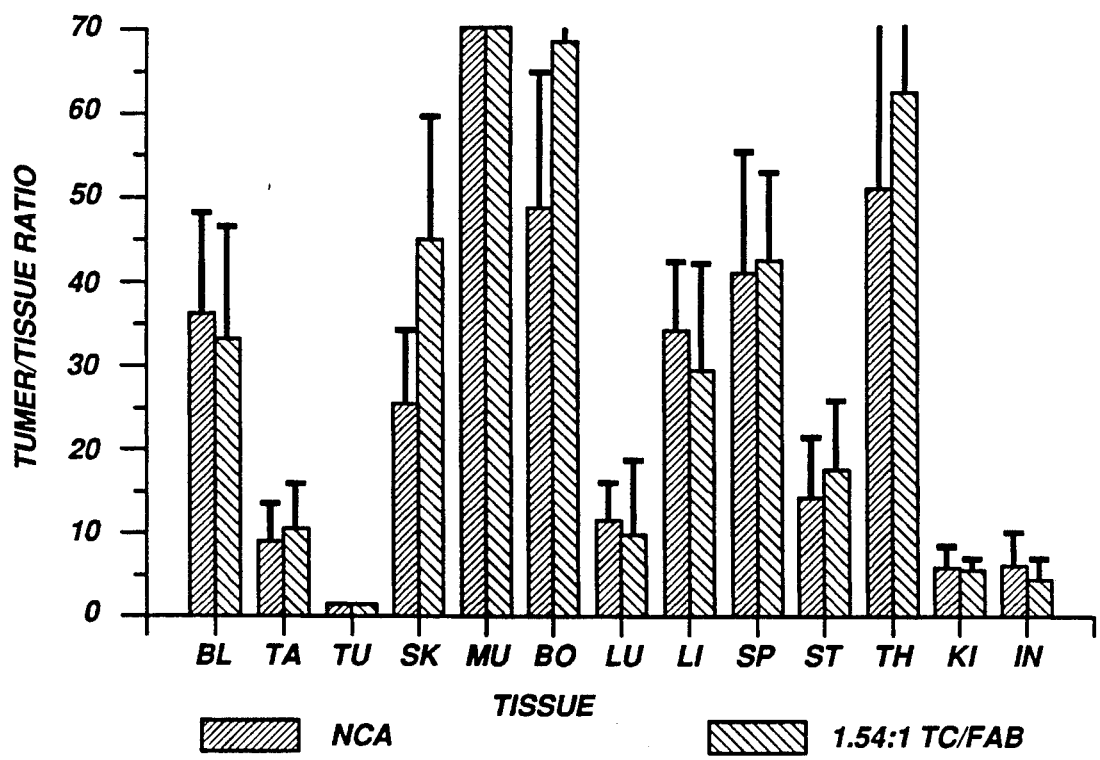
Figure 5:
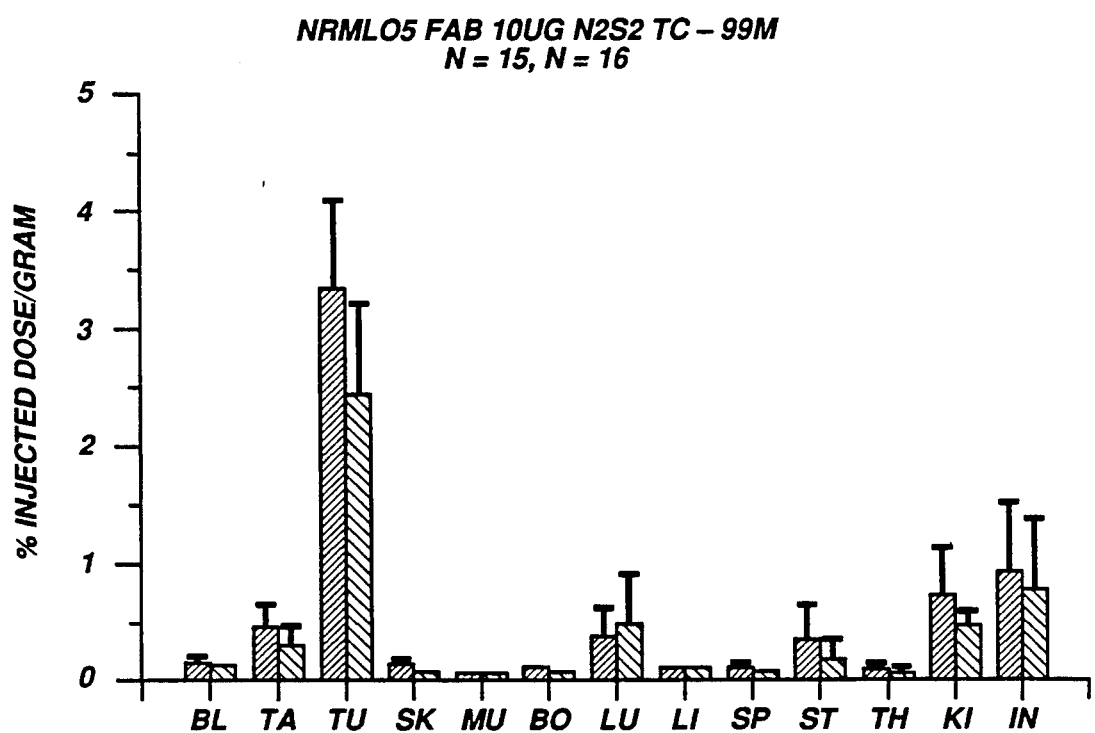
FIG. 5 is a tumor and tissue distribution profile as in FIG. 4 for a larger number of nude mice to lower the error of the statistical calculations. The molar ratios of no carrier added and 1.54:1 were tested.

This example illustrates the importance of the molar ratio of the label moiety to the targeting protein with an in vivo mouse study at four different molar ratios. A nude mouse bearing A375 melanoma xenografts was used as a model to assess tumor uptake of the minimally derivatized Tc-$N_2S_2$ label moiety NR-ML-05 fragment conjugate. A progressive loss in tumor uptake was observed in FIG. 4. The differences between the molar ratios of NCA and 1.4:1 of Tc-$N_2S_2$ to Fab antibody fragment are small when assessed by HPLC gel filtration (FIGS. 1 and 2) and in immunoreactivity (FIG. 3), thus an additional study was conducted with 15 nude mice at the NCA molar ratio and 16 mice at the 1.54:1 molar ratio of Tc-$N_2S_2$-Fab antibody fragment for in vivo tumor uptake. FIG. 5 shows the organ and tumor uptake results of this in vivo study.

EXAMPLE 4

This example illustrates a minimal derivatization process for iodine radionuclides. Iodine radionuclides are generally produced at relatively high specific activites. I-123 has a 13-hour half-life with 159 keV gamma radiation, I-125 has a 60.2-day half-life with 25 and 35 keV X-Ray and gamma photons, and I-131 has a 8.05-day half-life with 0.806 MeV beta maximum energy and 364 keV gamma of high abundance. Iodine-123 is typically found at very high specific activity levels, while I-125 and 1-131 are available at lower specific activity levels. Accordingly, the molar ratios can be adjusted with any of the three iodine radionuclides to produce an average of less than one iodine radionuclide or iodine label moiety per protein molecule.

Four molar ratios each of the label moiety I-125PIP and chloramine-T (CH-T) -I-125 were conjugated to NRML-05 whole antibody The immunoreactivity of the conjugated were compared with different molar ratios.

TABLE I

| PIP Molar Ratio | % IR | CH-T Molar Ratio | % IR |
| --- | --- | --- | --- |
| 0.1:1 | 78 | 0.1:1 | 79 |
| 0.6:1 | 79 | 0.9:1 | 77 |
| 1.1:1 | 80 | 1.3:1 | 75 |
| 2.7:1 | 70 | 5.3:1 | 55 |

Although the foregoing invention has been described, in part, by way of illustration and examine for the purposes of clarity and understanding, it will be apparent that certain changes or modifications may be practiced without deviating from the spirit and scope of the invention.

We claim:

1. A process for conjugating a targeting protein with a radiolabeled ligand, comprising the steps of:
    attaching unradiolabeled ligands to an insoluble support;
    reacting the ligands attached to the insoluble support with a radionuclide, wherein binding of the radionuclide by the ligand releases radiolabeled ligands from the insoluble support, while unradiolabeled ligands remain attached to the insoluble support; and
    conjugating the radiolabeled ligands with a targeting protein.

2. The process of claim 1 wherein the predominant species of conjugated targeting protein is a protein molecule having only one radiolabeled ligand per targeting protein molecule.

3. The process of claim 1 wherein a group attached to a sulfur donor atom on the unradiolabeled ligand reacts with the insoluble support to attach the unradiolabeled ligand to the insoluble support.

4. The process of claim 1 wherein a group attached to the insoluble support is a ligand substituent that is displaced by the radionuclide when the radionuclide is bound by the ligand, thereby causing release of radiolabeled ligands from the insoluble support.

5. The process of claim 1 wherein the solid support is selected from the group consisting of agarose, cellulose, latex, silica, polymers, and derivatives thereof.

6. A process for conjugating a targeting protein with a radiolabeled ligand, comprising the steps of:
    reacting a radionuclide with a ligand to produce a radiolabeled ligand, wherein a protein conjugation group is formed on the radiolabeled ligand during the radiolabeling reaction; and conjugating the radiolabeled ligand with a targeting protein.

7. The process of claim 6 wherein the predominant species of conjugating targeting protein is a protein molecule having only one radiolabeled ligand per targeting protein molecule.

8. The process of claim 1 or 6 wherein the targeting protein is selected from the group consisting of antibodies, antibody fragments, monoclonal antibodies, monoclonal antibody fragments, serum proteins, fibrinolytic enzymes, peptide hormones, biologic response modifiers, erythropoietin,, and mixtures thereof.

9. The process of claim 8 wherein the targeting protein is a monoclonal antibody or monoclonal antibody fragment.

10. The process of claim 8 wherein the targeting protein is a biologic response modifier.

11. The process of claim 10 wherein the biologic response modifier is selected from the group consisting of lymphokines, interferons, and colony-stimulating factors.

12. The process of claim 1 or 6 wherein the radionuclide is selected from the group consisting of TC-99m, I-123, Cu-64, Cu-67, Ga-67, Ga-68, Zr-89, In-111, I-131, Ru-97, Pb-203, Sn-177m, Rh-105, I-125, Re-186, Re-188, Au-199, At-211, Br-76, Br-77, F-18, B-206, Bi-212, and combinations thereof.

* * * * *

UNITED STATES PATENT AND TRADEMARK OFFICE
CERTIFICATE OF CORRECTION

PATENT NO.   :   5,059,541

DATED        :   October 22, 1991

INVENTOR(S)  :   Fritzberg et al.

It is certified that error appears in the above-identified patent and that said Letters Patent is hereby corrected as shown below:

In column 18, line 22 [claim 8], please delete the second comma.

In column 18, line 34 [claim 12], please change "TC" to --Tc--.

In column 18, line 37 [claim 12], please change "B-206" to --Bi-206--.

Signed and Sealed this

Thirty-first Day of October 1995

*Attest:*

BRUCE LEHMAN

*Attesting Officer*   Commissioner of Patents and Trademarks